(12) United States Patent
Grittke et al.

(10) Patent No.: US 8,499,641 B2
(45) Date of Patent: Aug. 6, 2013

(54) APPARATUS FOR DETERMINING AND/OR MONITORING ( {A} ) PRESSURE

(75) Inventors: Udo Grittke, Steinen (DE); Sergej Lopatin, Lorrach (DE); Andreas Roßberg, Bad Sackingen (DE); Thomas Uhlin, Schopfheim (DE); Axel Humpert, Reinau (DE); Andreas Spitz, Schopfheim (DE); Peter Selders, Maulburg (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 61 days.

(21) Appl. No.: 13/127,510

(22) PCT Filed: Oct. 27, 2009

(86) PCT No.: PCT/EP2009/064129
§ 371 (c)(1),
(2), (4) Date: Jul. 19, 2011

(87) PCT Pub. No.: WO2010/052152
PCT Pub. Date: May 14, 2010

(65) Prior Publication Data
US 2011/0265573 A1 Nov. 3, 2011

(30) Foreign Application Priority Data
Nov. 4, 2008 (DE) .......................... 10 2008 043 467

(51) Int. Cl.
*G01L 9/00* (2006.01)

(52) U.S. Cl.
USPC .............................................. 73/717; 73/723

(58) Field of Classification Search
None
See application file for complete search history.

(56) References Cited

U.S. PATENT DOCUMENTS

2007/0073417 A1   3/2007   Hedtke

FOREIGN PATENT DOCUMENTS

| DE | 39 01 492 A1 | 1/1990 |
| DE | 101 27 634 A1 | 12/2002 |
| DE | 103 28 296 A1 | 1/2005 |
| DE | 103 42 368 A1 | 4/2005 |
| DE | 10 2004 033 956 A1 | 2/2006 |
| DE | 10 2005 009 851 A1 | 9/2006 |
| DE | 10 2005 015 546 A1 | 10/2006 |
| DE | 10 2005 055 285 A1 | 5/2007 |
| DE | 10 2007 016 792 A1 | 10/2008 |
| DE | 10 2007 046 016 A1 | 4/2009 |

OTHER PUBLICATIONS

English translation of the International Preliminary Report.
International Search Report.
German Search Report.

*Primary Examiner* — Andre Allen
(74) *Attorney, Agent, or Firm* — Bacon & Thomas, PLLC

(57) ABSTRACT

An apparatus for determining and/or monitoring pressure. The apparatus comprises at least one pressure transducer, which transduces pressure into an electrical signal. The invention includes the features that at least one acoustic sensor is provided, that the acoustic sensor registers acoustic signals and transduces such into electrical signals, and that the acoustic sensor is mechanically and/or acoustically coupled with the pressure transducer.

5 Claims, 1 Drawing Sheet

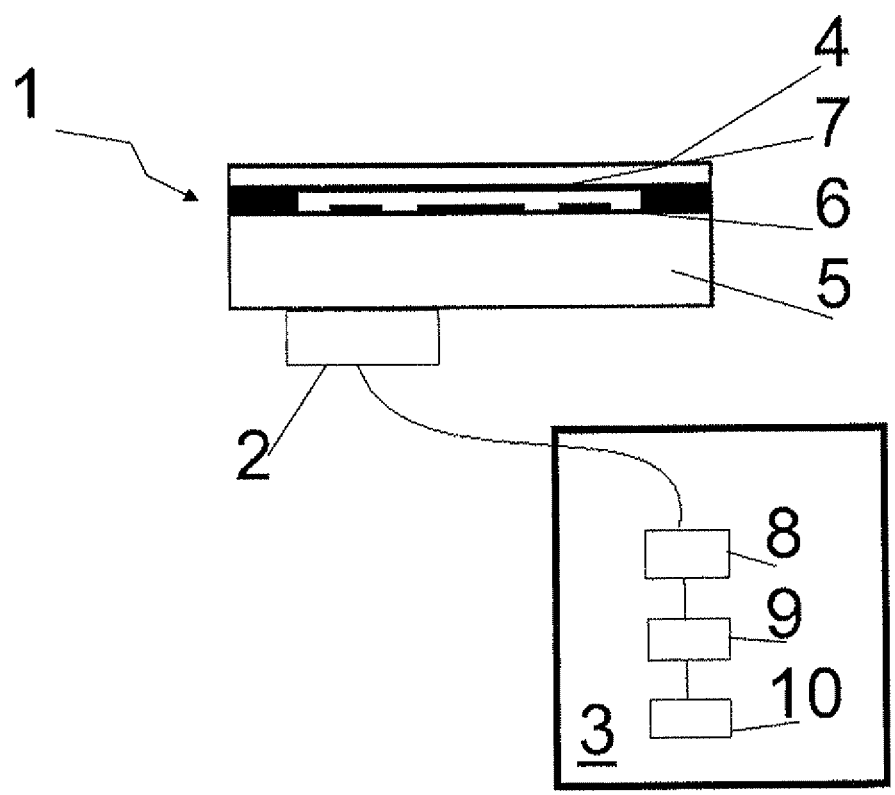

APPARATUS FOR DETERMINING AND/OR MONITORING ({A}) PRESSURE

TECHNICAL FIELD

The invention relates to an apparatus for determining and/or monitoring pressure, wherein the apparatus includes at least one pressure transducer, which transduces pressure into an electrical signal. Furthermore, the invention relates to an apparatus for determining and/or monitoring a process variable, wherein the apparatus includes at least one sensor unit, which determines and/or monitors the process variable.

BACKGROUND DISCUSSION

Pressure measuring apparatuses are often applied in process measurements technology, in order to measure the pressure of process media, which can be liquids, gases or vapors. Such measuring devices or pressure sensors essentially comprise a pressure measuring cell or a pressure transducer, which generally has a platform and an elastic membrane. The platform and the membrane are, depending on embodiment, composed of ceramic, or at least the membrane is at least partially composed of metal. Possible combinations of membrane and platform are, for example, ceramic/ceramic, metal/ceramic or metal/metal, with dielectric elements composed of ceramic or glass. The method for soldering metal onto ceramic is known, and can, for example, be implemented for the combination, titanium/aluminum oxide ceramic (or with special alloys, such as Kovar, in the place of the titanium). A dielectric ceramic of aluminum titanate with very low coefficient of expansion can, for example, also be combined with a nickel alloy, Invar, or a silicon carbide ceramic in the soldering method. Another embodiment has a stainless steel membrane welded onto a stainless steel platform. In the platform, a space for an insulating element for the measuring electrodes is preferably provided in the case of this embodiment. On the platform, a shallow cavity is most often provided, which is also referred to as a membrane bed, and is covered by the membrane. In measurement operation, the membrane is contacted with the pressure of the process medium, and the deformation or the mechanical stress in the elastic membrane, which, for example, is capacitively or piezo resistively ascertained, is a measure for the pressure (see e.g. Offenlegungsschrift DE 39 01 492).

In the case of ceramic cells of such pressure transmitters, crack formation in the membrane can be a cause for a failure of the cell. The thickness of such membranes is dependent on the measuring range of the pressure, and most often lies, for instance, between 0.1 and 2 mm. It is known that, in contrast to metals, ceramic materials, due to their brittleness and the lack of plastic deformability resulting therefrom, can break very quickly when the mechanical stress reaches the ultimate tensile strength. The cause for a breaking of the membrane can be microscopic cracks in the ceramic, which, under a load, have reached an over-critical growth. In the case of some manufacturing steps, e.g. working the material (for instance machining the material) while it is hard, cracks can be caused, which, however, cannot be recognized due to their small size. Another cause for critical crack growth can be a local overloading of the components due to an unfavorable combination of thermal gradients during a temperature shock in the case of a simultaneous pressure or vacuum loading. The measuring cells can thus be mechanically and thermally overloaded in applications, and, react thereto with crack growth. In the extreme case, cracks are recognized through leakage associated therewith, whereby to some degree complex maintenance measures are required. In the case of metal membranes, it is furthermore possible that, due to excessive pressure, a plastic deformation will occur, which leads to a marked measurement deviation. In the state of the art, for detecting membrane breakage, the application of, for example, a sacrificial membrane is provided, which is damaged by a corrosive attack or other critical events. The failure of the sacrificial cell serves as a sign that the measuring cell is also damaged or is shortly about to become damaged.

SUMMARY OF THE INVENTION

An object of the invention is to provide a pressure transmitter, in the case of which a breaking of the membrane or a plastic deformation can be recognized.

The object is achieved according to the invention by features including that at least one acoustic sensor is provided, the acoustic sensor registers acoustic signals and transduces them into electrical signals, and the acoustic sensor is mechanically and/or acoustically coupled with the pressure transducer. In the pressure transmitter of the invention, an already known pressure sensor is thus supplemented with an acoustic sensor. The pressure transducer is, in such case, at least partially composed of ceramic and/or of metal. In such case, via the additional sensor, an acoustic diagnostic procedure is performed, which concerns itself either with breakage or with plastic deformation. It has especially been found that ceramic materials such as aluminum oxide ceramic or zirconium oxide ceramic produce clear acoustic signals shortly before a complete breaking of a membrane. Such signals come from microscopic fractures in the ceramic grains and, according to the invention, are registered with an acoustic sensor. The frequency of the signals can lie in a range of between 50 kHz and 3 MHz. In an embodiment, the acoustic sensor is secured on the platform of the pressure transducer. The actual securement position of the acoustic sensor is non-critical, since, especially in the case of a ceramic platform, the acoustic signals of the named frequencies propagate well in such a ceramic body.

In an embodiment, at least one evaluation unit is provided, and the evaluation unit evaluates the electrical signals of the acoustic sensor.

Another embodiment includes that the pressure transducer has at least one membrane, which is contactable with pressure. During use, the membrane is thus exposed to the process pressure to be measured, or to the medium. In an embodiment, the membrane is, in such case, especially composed of a ceramic. In an additional embodiment, the membrane is composed of a metal.

An embodiment provides that the evaluation unit evaluates the electrical signals of the acoustic sensor toward detecting a breaking of the membrane of the pressure transducer. This embodiment especially relates to a ceramic membrane.

An embodiment provides that the evaluation unit evaluates the electrical signals of the acoustic sensor toward detecting a plastic deformation of the membrane of the pressure transducer. This embodiment especially relates to a metal membrane.

In such case, the evaluation unit is, in an embodiment, a component of the electronics, with which the pressure transducer is connected. The evaluation unit can, however, also be a superordinated unit, e.g. within a control room. In an embodiment, the signals and/or their Fourier transformed spectra are evaluated as regards the occurring frequencies and/or signal groups and/or individual signals.

An embodiment includes that the evaluation unit evaluates the electrical signals of the acoustic sensor in such a manner, that the evaluation unit detects, and marks as indicative of breaking or plastic deformation of the membrane, at least the occurrence of at least one characteristic frequency and/or at least one characteristic signal group and/or at least one characteristic individual signal in the electrical signals of the acoustic sensor. As already described above, breaks in the membrane or the plastic deformation of the latter lead especially to signals that are registered by the acoustic sensor. These signals are distinguished within the electronic signals of the acoustic sensor by, for example, characteristic frequencies or characteristic signal groups or characteristic single signals. The electronic (measuring-) signals of the acoustic sensor are, in such case, evaluated, for example, via Fourier transformation, or in connection with a bandpass filter. In the case of the Fourier transformation, there thus results from the signal of the acoustic sensor a spectrum, in which characteristic signals or frequencies are searched for. The spectrum must include short signals with a certain duration. The micro cracking does not last long, and its duration corresponds to the above named frequencies of 50 kHz to 3 MHz. Since the normal environmental noise signals in this frequency range are most often very weak, the strong characteristic signals can thereby be detected and evaluated.

An embodiment provides that the evaluation unit evaluates the time behavior of the electrical signals of the acoustic sensor. In this embodiment, the signals of the acoustic sensor are evaluated for a prediction, that is in the sense of predictive maintenance, i.e. the individual signals of the acoustic sensor are evaluated with regard to time developments or tendencies. In such case, in an embodiment, the electrical signals themselves are evaluated, and in an additional embodiment, characteristic single signals or signal groups are evaluated and assessed with regard to development as a function of time.

An embodiment includes that the pressure transducer has at least one platform, that the membrane is connected with one side of the platform, and that the acoustic sensor is placed on a side of the platform facing away from the membrane.

An embodiment provides that the pressure transducer is a capacitive pressure transducer.

Furthermore, the invention relates to an apparatus for determining and/or monitoring a process variable, wherein the apparatus has at least one sensor unit, which determines and/or monitors the process variable, and wherein the apparatus is embodied in such a manner, that at least one acoustic sensor is provided, that the acoustic sensor registers acoustic signals and transduces them into electrical signals, and that the acoustic sensor is mechanically and/or acoustically coupled with the sensor unit. In such case, this thus generally involves a measuring device for a process variable, e.g. pressure, density, viscosity, fill level, pH value, etc., whose sensor unit is monitored by an acoustic sensor. Correspondingly, the embodiments described above, wherein a breaking or deformation of the sensor unit is quite generally deduced from measurement signals of the acoustic sensor, hold for this apparatus.

BRIEF DESCRIPTION OF THE DRAWING

The invention will now be explained in greater detail on the basis of the appended drawing, the sole FIGURE of which shows as follows:

FIG. 1 is a schematic representation of a pressure measuring device of the invention.

DETAILED DISCUSSION IN CONJUNCTION WITH THE DRAWING

FIG. 1 shows schematically a ceramic pressure transducer 1, to whose ceramic platform 5 an acoustic sensor 2 is applied. In this embodiment, pressure transducer 1 uses the capacitive pressure measurement principle. Thus, the process pressure acting on the ceramic membrane 4 changes the distance between the measuring electrodes 6 and the counterelectrode 7, in order to influence the capacitances of the corresponding capacitors.

Acoustic sensor 2 measures especially sound in the form of body waves propagated through the platform 5, and produces electrical (measurement) signals therefrom, which are evaluated by the evaluation unit 3.

Evaluation unit 3 here includes at least the following components: A bandpass filter 8, which in these embodiments only lets through frequencies within a band between 50 kHz and 3 MHz, and filters out extraneous signals; an amplifier 9, which amplifies and conditions the filtered signals; and, finally, for example, an analog-digital converter and a microprocessor 10, which serves as a detector of the acoustic emission and, according to particular rules, detects the acoustic emission in the ceramic cell and, for example, activates an alarm output.

LIST OF REFERENCE CHARACTERS 1 pressure transducer
2 acoustic sensor
3 evaluation unit
4 membrane
5 platform
6 measuring electrode
7 counterelectrode
8 bandpass
9 amplifier
10 microprocessor

The invention claimed is:

1. An apparatus for determining and/or monitoring pressure, comprising:
at least one pressure transducer, which transduces pressure into an electrical signal;
at least one acoustic sensor; and
at least one evaluation unit, wherein:
said acoustic sensor registers acoustic signals and transduces them into electrical signals;
said acoustic sensor is mechanically and/or acoustically coupled with said pressure transducer;
said evaluation unit evaluates said electrical signals of said acoustic sensor;
said pressure transducer has at least one membrane, which is contactable with pressure; and
said evaluation unit evaluates electrical signals of said acoustic sensor toward detecting a breaking or plastic deformation of said at least one membrane of said pressure transducer.

2. The apparatus as claimed in claim 1, wherein:
said evaluation unit evaluates electrical signals of said acoustic sensor in such a manner that said evaluation unit detects, and marks as a breaking or plastic deformation of said at least one membrane, at least occurrence of at least one characteristic frequency and/or at least one characteristic signal group and/or at least one characteristic individual signal in electrical signals of said acoustic sensor.

3. The apparatus as claimed in claim 1, wherein:
said evaluation unit evaluates behavior of electrical signals of said acoustic sensor as a function of time.

4. The apparatus as claimed in claim 1, wherein:
said pressure transducer has at least one platform, said membrane is connected with one side of said platform, and said acoustic sensor is placed on a side of said platform facing away from said at least one membrane.

5. The apparatus as claimed in claim 1, wherein:
said pressure transducer is a capacitive pressure transducer.

* * * * *